(12) United States Patent
Grätz

(10) Patent No.: US 6,508,649 B2
(45) Date of Patent: Jan. 21, 2003

(54) DENTAL TOOL

(75) Inventor: Dieter Grätz, Au (CH)

(73) Assignee: Edenta AG Dentalprodukte Switzerland, Au (CH)

( * ) Notice: Subject to any disclaimer, the term of this patent is extended or adjusted under 35 U.S.C. 154(b) by 0 days.

(21) Appl. No.: 09/891,302

(22) Filed: Jun. 27, 2001

(65) Prior Publication Data
US 2002/0119421 A1 Aug. 29, 2002

(30) Foreign Application Priority Data
Feb. 27, 2001 (DE) .......................... 101 09 321

(51) Int. Cl.$^7$ .................................. A61C 3/06
(52) U.S. Cl. ...................................... 433/142
(58) Field of Search ................. 433/142, 143, 433/144, 166; 132/75.6, 76.4, 321, 329; 451/526

(56) References Cited

U.S. PATENT DOCUMENTS

| | | | | |
|---|---|---|---|---|
| 4,270,903 A | * | 6/1981 | Nash | 433/165 |
| 4,830,615 A | * | 5/1989 | Feinman et al. | 433/142 |
| 5,063,118 A | | 11/1991 | Goetz | |
| 5,476,381 A | * | 12/1995 | Dragan | 30/169 |
| 5,836,810 A | * | 11/1998 | Asum | 433/142 |

FOREIGN PATENT DOCUMENTS

| | | | |
|---|---|---|---|
| CH | 117888 | 12/1926 | |
| EP | 0 354 870 A2 | 7/1989 | |
| GB | 2059266 A | * 4/1981 | A61C/15/00 |

OTHER PUBLICATIONS

English translation of HOPF, Paul 117888 patent.

* cited by examiner

Primary Examiner—Kevin Shaver
Assistant Examiner—Melba Bumgarner
(74) Attorney, Agent, or Firm—Laurence E. Laubscher, Sr.

(57) ABSTRACT

In a dental tool in the form of a strip for the abrasion of a tooth and/or tooth filling material, a diamond coating provided on at least one lateral face of the strip, and a tooth system being provided on at least one edge thereof.

16 Claims, 3 Drawing Sheets

DENTAL TOOL

BACKGROUND OF THE INVENTION

1. Field of the Invention

The invention relates to a dental tool or implement a for the abrasion of a tooth and/or tooth filling material.

2. Brief Description of the Prior Art

In the case of damage to teeth, which can be caused by caries, accidents or the use of force, the resulting cavities are filled with filling material. The filling material then has to undergo further abrasion and finally the surface of the filling material is made as smooth as possible, because a rough surface would form retention points for bacteria.

The rotary tools conventionally used for the smoothing of the dental material only extend to a limited extent into the gap between two teeth. So that a smooth surface can also be created in the interdental space, use is normally made of metal strips. In a first treatment step use is made of a strip with a sawtooth system, in order to create a gap between the tooth with the filling and the neighboring tooth. In a second treatment step use is made of a strip with a diamond coating. By reciprocating the diamond strip backwards and forwards in the gap the tooth and/or filling material surface is smoothed. Use can be made of several metal strips with different diamond coating grain size in order to achieve the desired, smooth surface structure.

However, the changing of the dental strip used for a specific treatment step leads to a danger of the strips hooking or jamming on insertion and removal and in certain circumstances this can cause injury to the person being treated.

SUMMARY OF THE INVENTION

The problem of the invention is to provide a dental tool, with which a faster and safer treatment of the interdental space between two teeth can be obtained than with know dental tools.

In the case of the dental tool according to the present invention, the sawtooth system producing a gap as well as the diamond coating provided for smoothing the surface are combined into a single tool, which simplifies the injury-free production of smooth surfaces in the interdental space.

A preferred dental tool according to the present invention can have a first and a second diamond coating portion on the lateral face or faces of the strip, which are separated by a tooth system portion. The tooth system preferably only extends over the length of the tooth system portion, i.e. over the length of the intermediate area of the strip separating both diamond coating portions. However, the tooth system can also extend over the entire strip length and preferably in the first mentioned variant it is diamond coating-free.

The edges of the strip are preferably not diamond-coated. This makes it possible to manufacture the strip from an already diamond-coated metal band by cutting, e.g. using a laser.

The diamond coating can have in different diamond coating portions different diamond coating grain sizes in the grain diameter range 8 to 150 µm.

The working procedure is e.g. as follows when using a dental tool according to the invention which, apart from a diamond coating on the lateral faces, has a tooth system along one edge. The strip is introduced beforehand into the dental gar, between two teeth using the toothed edge and filling or dental material is removed from the gap by a sawing movement. The strip is then removed from the dental gap and reintroduced turned by 180°, so that the tooth system points away from the base of the dental gap. Using the diamond-coated lateral face portions of the strip, now the gap lateral faces are ground and therefore smoothed by drawing the strip backwards and forwards through the interdental space and whilst exerting a gentle lateral pressure.

BRIEF DESCRIPTION OF THE DRAWINGS

Further advantageous developments of the invention are described in greater detail hereinafter with reference to the accompanying drawings, in which.

DETAILED DESCRIPTION

Figure 1:
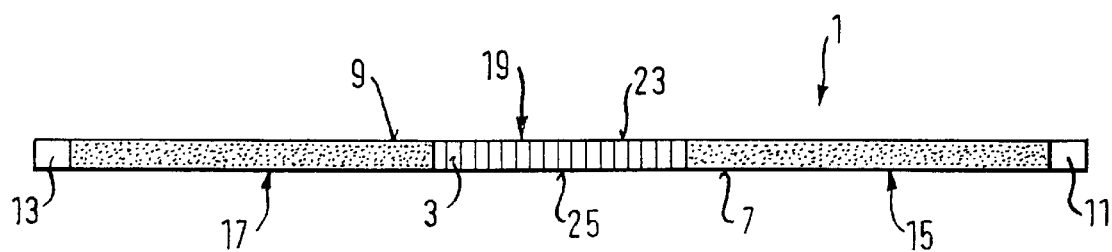
FIG. 1 is a plan view of a first embodiment of a dental tool according to the present invention.
Figure 2:
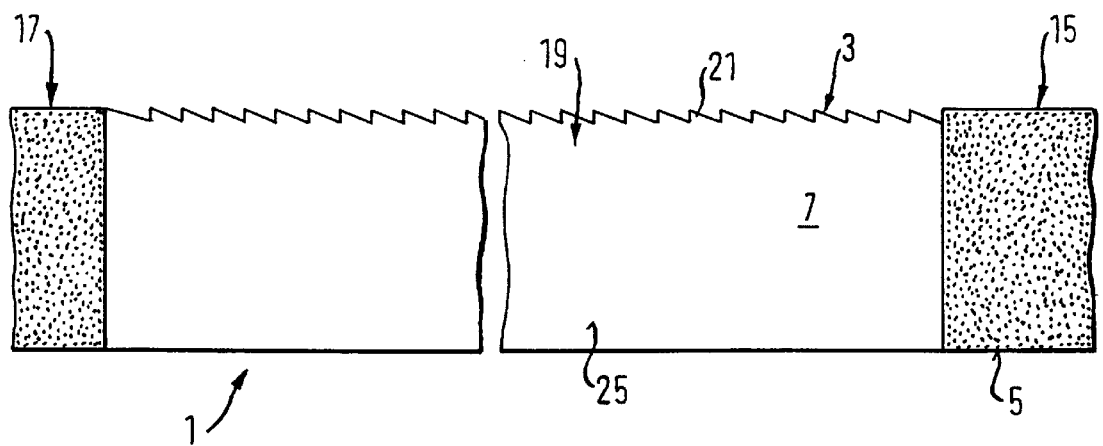
FIG. 2 is a partial side view of the embodiment of FIG. 1 at a larger scale.

The dental tool or implement 1 shown in FIGS. 1 and 2 comprises a strip of a hard, corrosion-resistant metal, e.g. stainless steel, titanium, etc. with two parallel edges 3, 5 and two parallel lateral faces 7, 9.

On each of its two free ends the dental tool 1 has a gripping portion 11, 13 for a secure gripping and handling of said dental tool 1, a first and a second diamond coating portion 15, 17, in each case having a diamond coating on one or both lateral faces 7, 9 of the strip and an intermediate, diamond coating-free tooth system portion 19, having on an edge 3 a series of sawteeth 21.

The tooth system portion 19 comprises two smooth, diamond coating-free lateral face portions 23, 25, which are laterally bounded by the diamond coated portions 15, 17. Sawteeth 21 extend between the diamond coated portions 15, 17 on one edge of the tooth system portion and said sawteeth 21 are not diamond coated.

As a result of the diamond coating-free faces 23, 25 of the tooth system portion 19 it is easy to work with the dental tool 1, because on sawing the strip 1 does not stick laterally on the teeth of the patient and can instead slide backwards and forwards without hindrance.

In addition, in the vicinity of the tooth system portion 19, the strip 1 can be readily inserted into and removed again from the gap between two teeth of the patient without the strip hooking on the tooth sides.

Figure 3:
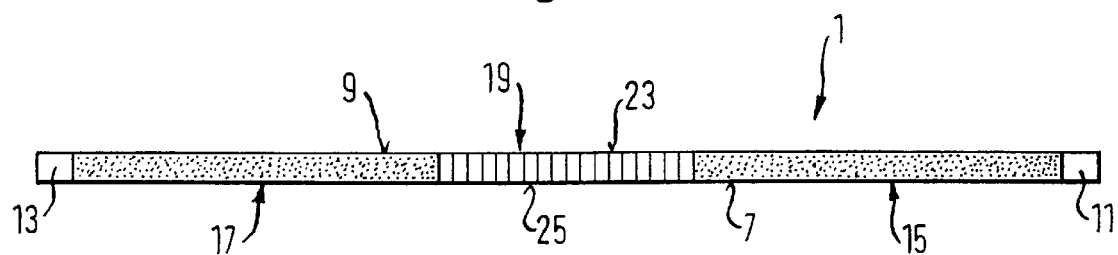
FIG. 3 is a plan view of a further embodiment of the dental tool according to the invention.
Figure 4:
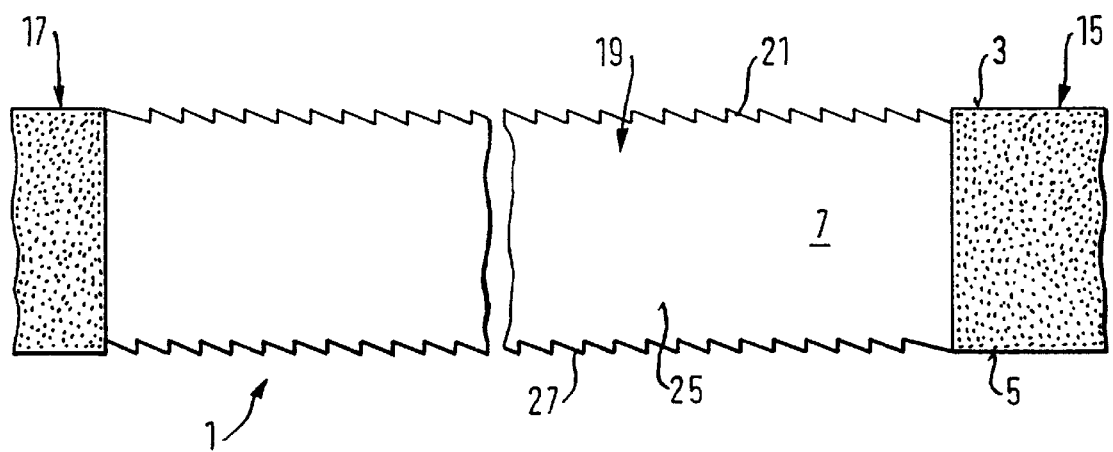
FIG. 4 is a partial side view of the embodiment of FIG. 3 at a larger scale.

In the construction according to FIGS. 3 and 4 identical or functionally identical components of the dental tool are given the same reference numerals and will not be described again. With the dental tool according to FIGS. 3 and 4 sawteeth 27 are also provided on the second longitudinal edge 5. The sawteeth 27 can have a finer or coarser tooth system than the sawteeth 21.

Figure 5:
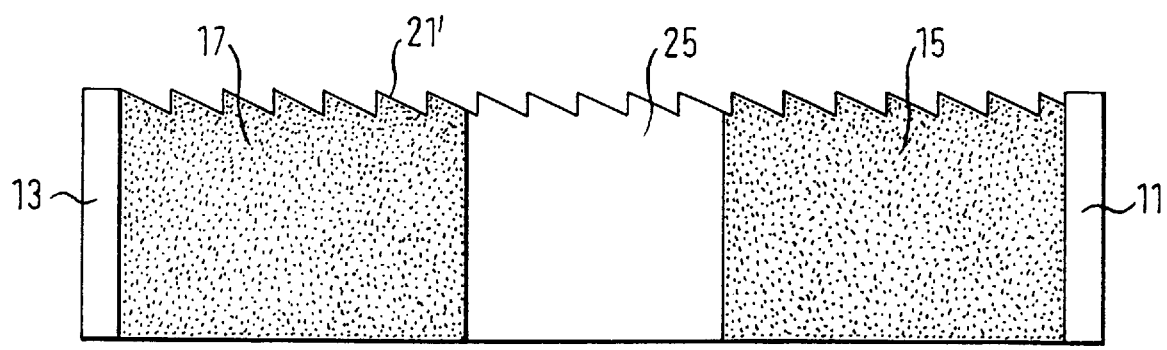
FIG. 5 is a side view of another embodiment of a dental tool according to the invention.

The embodiment of FIG. 5 is similar to that of FIG. 1. The only distinction is, that the sawteeth 21' extend over the whole length of the strip except the gripping portions 11, 13, that is over the diamond coating free portions 23, 25 and also over the diamond coating portions 15, 17.

Figure 6:
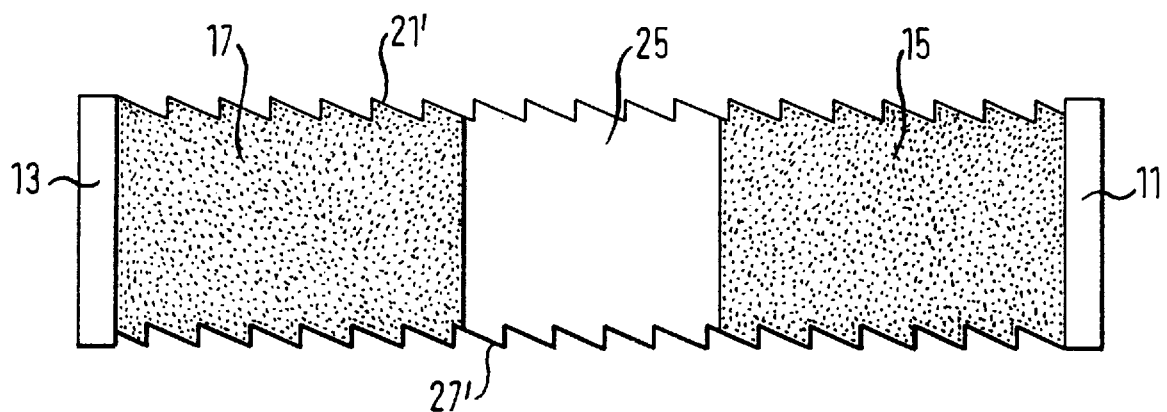
FIG. 6 a side view of still another embodiment of a dental tool according to the invention.

That is also true for the embodiment of FIG. 6, which is similar to FIG. 4. However, in the strip of FIG. 6 both series of sawteeth systems 21 and 27 extend over the whole strip length.

In practice, such a dental tool can have a length of 8 to 500 mm, preferably 5 to 100 mm, a width of 1 to 20 mm and a thickness of 0.01 to 1.0 mm. The diamond coating portions 15, 17 can have different diamond grain sizes. An average grain diameter is in the range 8 to 150 μm.

What is claimed is:

1. A dental tool in the form of a strip for the abrasion of a tooth or of a tooth filling material, comprising:

(a) a metal strip (1) having a pair of lateral surfaces (7, 9) and a pair of longitudinal edges (3, 5);

(b) a first diamond coating arranged on a first portion (15) of one of said lateral surfaces (7), said one lateral surface also having an uncoated diamond-free second portion (25); and (c) a first sawtooth system (21) extending longitudinally at least partially on one of said strip edges.

2. A dental tool in the form of a strip for the abrasion of a tooth or a tooth filling material as defined in claim 1, and further including:

(d) a second diamond coating (17) arranged on a third portion of said one lateral surface, said uncoated diamond-free portion (25) being arranged between said first and second diamond coatings portions.

3. Dental tool according to claim 2, wherein said sawtooth system extends over the total length of said strip.

4. Dental tool according to claim 2, wherein the sawtooth system extends over the length of said uncoated diamond-free second portion.

5. Dental tool according to claim 2, wherein the edges of the strip are free from a diamond coating.

6. Dental tool according to claim 2, wherein said sawtooth system is free from a diamond coating.

7. Dental tool according to claim 2, wherein said first and second coatings comprise different diamond coating grain sizes.

8. Dental tool according to claim 2, wherein the average diameter of a diamond coating grain is between 8 and 150 μm.

9. Dental tool according to claim 2, wherein the strip length is between 5 and 100 mm.

10. Dental tool according to claim 1, wherein said sawtooth system extends over the total length of said strip.

11. Dental tool according to claim 1, wherein the sawtooth system extends over the length of said uncoated diamond-free second portion.

12. Dental tool according to claim 1, wherein the edges of the strip are free from a diamond coating.

13. Dental tool according to claim 1, wherein said sawtooth system is free from a diamond coating.

14. Dental tool according to claim 1, wherein said first diamond coating comprises different diamond coating grain sizes.

15. Dental tool according to claim 1, wherein the average diameter of a diamond coating grain is between 8 and 150 μm.

16. Dental tool according to claim 1, wherein the strip length is between 5 and 100 mm.

* * * * *